United States Patent
Nakaguchi et al.

(10) Patent No.: US 9,460,637 B2
(45) Date of Patent: Oct. 4, 2016

(54) STETHOSCOPY TRAINING SYSTEM AND SIMULATED STETHOSCOPE

(75) Inventors: Toshiya Nakaguchi, Chiba (JP); Masahiro Tanabe, Chiba (JP)

(73) Assignees: National University Corporation Chiba University, Chiba (JP); Kenzmedico Co., Ltd., Saitama (JP)

( * ) Notice: Subject to any disclaimer, the term of this patent is extended or adjusted under 35 U.S.C. 154(b) by 456 days.

(21) Appl. No.: 14/235,018

(22) PCT Filed: May 11, 2012

(86) PCT No.: PCT/JP2012/062218
§ 371 (c)(1),
(2), (4) Date: May 20, 2014

(87) PCT Pub. No.: WO2012/160999
PCT Pub. Date: Nov. 29, 2012

(65) Prior Publication Data
US 2014/0302473 A1    Oct. 9, 2014

(30) Foreign Application Priority Data

May 26, 2011    (JP) .................................. 2011-117530

(51) Int. Cl.
G09B 23/28    (2006.01)

(52) U.S. Cl.
CPC .............. *G09B 23/28* (2013.01); *G09B 23/285* (2013.01)

(58) Field of Classification Search
CPC .... G09B 23/28; G09B 23/36; G06F 19/3437
See application file for complete search history.

(56) References Cited

U.S. PATENT DOCUMENTS

| 8,882,511 | B2 | 11/2014 | McKenzie et al. | |
| 2007/0122785 | A1* | 5/2007 | Eggert | G06F 19/3437 434/272 |
| 2009/0305212 | A1 | 12/2009 | McKenzie et al. | |
| 2010/0292010 | A1 | 11/2010 | Kira et al. | |

FOREIGN PATENT DOCUMENTS

| JP | 2005-077521 | 3/2005 |
| JP | 2005-227534 | 8/2005 |
| JP | 2010-264171 | 11/2010 |

OTHER PUBLICATIONS

International Search Report mailed Jul. 31, 2012 in Application No. PCT/JP2012/062218.
Notice of Reasons for Refusal mailed Mar. 3, 2015 in Application No. 2011-117530.

\* cited by examiner

*Primary Examiner* — Timothy A Musselman
(74) *Attorney, Agent, or Firm* — Knobbe, Martens, Olson & Bear LLP

(57) ABSTRACT

Provided is a stethoscopy training system which is inexpensive and has a simple configuration, without using a device which measures a respiratory operation of a simulated patient. The stethoscopy training system for this objective is formed from: a simulated stethoscope (1) having a sound acquisition unit further comprising a location display means (1*d*), a tube, and ear pipes; a location sensing means (2) for sensing the location of the sound acquisition unit; biological sound database (3); a biological sound reproducing means (4); and a timing display means (5) for displaying a timing of a repetition of a reproduced respiratory sound. The database retains as information biological sounds which are prerecorded from actual patients in correspondence with chest locations. The biological sound reproducing means further comprises a voice reproducing apparatus (4*a*), extracts prescribed biological sound information from the database according to the sound acquisition unit location which the location sensing means has sensed, and emits a reproduced biological sound from the voice reproducing apparatus, which a trainee hears via the ear pipes. The simulated patient views the timing display means and matches his or her respiratory operation to a reproduced respiratory sound.

14 Claims, 7 Drawing Sheets

STETHOSCOPY TRAINING SYSTEM AND SIMULATED STETHOSCOPE

REFERENCE TO RELATED APPLICATIONS

This application is the U.S. National Phase of International Application PCT/JP2012/062218, filed May 11, 2012, and claims priority to JP Application No.2011-117530, filed May 26, 2011. Each of the priority applications is hereby incorporated by reference in its entirety.

TECHNICAL FIELD

The present invention relates to a stethoscopy training system and a simulated stethoscope.

BACKGROUND ART

When a patient visits a doctor to complain of symptoms, at a first time, a doctor asks a patent about his or her conditions to examine a physical finding, i.e., asks a clinical history and condition of the patent. At that time, as a part of a clinical examination, a doctor hears biological sound (respiratory sound, cardiac sound, bowel sound, etc.) by placing a stethoscope (exactly speaking, a sound acquisition unit) on the diseased part to diagnose name of disease and condition of the patient.

A stethoscope roughly comprises a sound acquisition unit, a tube (also called as "rubber tube"), and ear pipes.

However, a trainee such as a medical student aiming for a doctor and a nursing student aiming for a nurse should acquire skill for stethoscopy. Thus, stethoscopy training is in progress for a trainee. Conventionally, a doctor (a medical instructor) auscultates a patient in a sickroom and an outpatient. A textbook having a DVD supplement in which cardiac sound, respiratory sound, etc. are recorded is used. Thereafter, a study such as stethoscopy training is performed by exercising a trainee. However, there are problems that authenticity does not exist and patient has a burden, thereby a plurality of trainees is not capable of being trained. There is also problem that patients having a rare disease are few in number.

Thus, recently, a stethoscopy training system for virtual stethoscopy training has been employed. The stethoscopy training system roughly comprises a mannequin, biological sound database, and a biological sound reproducing device. Small-scaled speakers are embedded in a plurality of predetermined locations of a chest in a mannequin. A biological sound database previously retains biological sound recorded from corresponding predetermined location of a chest of an actual patient as information. A biological sound reproducing device extracts and reproduces predetermined biological sound information from biological sound database according to predetermined location to emit the reproducing biological sound from the small-scaled speakers. A medical instructor manipulates the system and trainees auscultate reproducing biological sound (normal sound and abnormal sound) emitted from the small-scaled speakers through stethoscope to respond name of disease. In some cases, stethoscopy training is performed by a medical instructor correcting the response. When correct answer is separately prepared, trainees are capable of being trained alone without a medical instructor.

In patent reference 1 described below, disclosed is a stethoscopy training system comprising a simulated stethoscope, a human body model, a stethoscopy detection sensor for detecting stethoscopy operation via the simulated stethoscope, a control unit for receiving detected signal produced from the detection sensor and reproducing biological sound from a stethoscopy location corresponding to the detected signal via biological sound reproducing unit that is formed in ear pipes unit of the simulated stethoscope.

In patent reference 2 described below, disclosed is a medical condition simulation system comprising a movable roaming device and a positioning device determining location information of the roaming device, wherein the location information is received to compare with regulated set of a previously provided region, and when the location information is identical to the regulated set, a computing device transmitting information that displays medical condition is used.

PRIOR ART REFERENCES

Patent References

Japanese Patent Application Laid-Open Publication No. 2005-077521
Japanese Patent Application Laid-Open Publication No. 2008-518277

DESCRIPTION OF THE INVENTION

Problems to be Solved by the Invention

Generally, stethoscopy training is performed by asking a patient about his or her condition and doing auscultation. In the stethoscopy training, a mannequin is used. However, when asking a patient about his or her condition, a mannequin is not used. Thus, when asking a patient about his or her condition, used is not an actual patient but a simulated patient. A simulated patient complains of his clinical history and condition of disease to a trainee by acting as an actual patient.

That is to say, a trainee asks a simulated patient about his or her condition and then auscultates a mannequin. However, in this method, a trainee feels uncomfortable because a simulated patient changes into a mannequin as a training object. Thus, authenticity for training becomes low. Furthermore, at the present time, a mannequin is extremely expensive. For example, the price of the mannequin is about six million yen for an American-made mannequin and about three million yen for a Japanese-made mannequin.

Skill disclosed in patent reference 1 uses a human body model. However, problems described above is not solved.

Skill disclosed in patent reference 2 is applied that a test subject may be a mannequin or a simulated patient (a standard patient). (See paragraph [0017].) Especially, a system disclosed in FIG. 6 detects predetermined location of a stethoscope on test subject, exactly speaking a sound acquisition unit (head piece) by using a camera and extracts biological sound corresponding to the predetermined location from sound file of computer to be capable of giving reproducing biological sound to a trainee via an earpiece of a stethoscope. (See paragraph [0033] and [0034].)

However, reproducing biological sounds includes respiratory sound and cardiac sound. When test subject performs respiratory motions of different timing compared to reproduced respiratory sound (reproducing respiratory sound), a trainee feels uncomfortable and training effect decreases.

Thus, in patent reference 2, a computer measures a timing for respiratory operation of a test subject to extend or reduce the timing for reproducing respiratory sound in accordance with the measured value. Moreover, reproducing respiratory sound is given to a trainee. (See paragraph [0030].)

However, a device measuring such timing for respiratory operation makes a system complex and expensive, thereby a system has not been practical use.

Furthermore, in patent reference 2, a location of a roaming device is three-dimensionally obtained. A system is designed to determine contact between a device and a test subject from location information. However, extremely high accuracy is required to determine the contact from location information, thereby error determination frequently occurs.

Thus, in order to solve the above-mentioned problem, the present invention provides a stethoscopy training system with simplicity and low cost.

Means for Solving the Problems

Herein, a stethoscopy training system according to one embodiment of the present invention comprising: a simulated stethoscope being provided with a sound acquisition unit, a tube and ear pipes; a location sensing means for sensing a location of the sound acquisition unit; a biological sound database; and a biological sound reproducing means, wherein when a trainee asks a simulated patient about his or her condition and auscultates the simulated patient by placing the sound acquisition unit on a chest of the simulated patient, the trainee hears a simulated biological sound reproduced from the biological sound reproducing means through the ear pipes, wherein the sound acquisition unit has a location display means for displaying its location, the location sensing means senses location where the sound acquisition unit is placed on a chest of the simulated patient by photographing the chest of the simulated patient and the location display means and performing image treatment, the biological sound database retains as information biological sounds containing respiratory sound and cardiac sound previously recorded in accordance with location of a chest of an actual patient, the biological sound reproducing means includes a voice reproducing apparatus attached to the simulated stethoscope, the biological sound reproducing means and the voice reproducing apparatus are wiredly and wirelessly connected, the biological sound reproducing means extracts predetermined biological sound information from the biological sound database corresponding to the location of the sound acquisition unit sensed by the location sensing means and emits reproduced biological sound from the voice reproducing apparatus, the emitted reproduced biological sound reaching ears of the trainee via the voice reproducing apparatus and the ears pipes, furthermore, the system comprises a timing display means for displaying a repetition of a timing of reproduced respiratory sound, the simulated patient can match his respiratory operation with timing of a respiratory sound in the reproduced biological sound by observing the timing display means.

Moreover, a stethoscopy training system according to another embodiment of the present invention comprising: A stethoscopy training system comprising: a simulated stethoscope being provided with a sound acquisition unit, a tube and ear pipes; a location sensing means for sensing a location of the sound acquisition unit; a biological sound database; a biological sound reproducing means; and a timing display means for displaying a repetition of a timing of reproduced respiratory sound, wherein the sound acquisition unit has its location display means for displaying a location, the location sensing means senses a location where a sound acquisition unit is placed on a chest of the simulated patient by photographing the chest of the patient and the location display means and performing image treatment, the biological sound database retains as information biological sounds containing respiratory sound and cardiac sound previously recorded in accordance with a location of a chest of an actual patient, the biological sound reproducing means includes a voice reproducing apparatus attached to the simulated stethoscope, the biological sound reproducing means and the voice reproducing apparatus are wiredly and wirelessly connected, the biological sound reproducing means extracts predetermined biological sound information from the biological sound database corresponding to the location of the sound acquisition unit sensed by the location sensing means and emits reproduced biological sound from the voice reproducing apparatus, the emitted reproduced biological sound reaching ears of the trainee via the voice reproducing apparatus and the ears, the timing displays means is formed so that the simulated patient can match his respiratory operation with timing of respiratory sound in the reproduced biological sound by observing the timing display means.

Furthermore, in the above embodiments, preferred embodiment is, but not limited, that the location display means is an infrared light LED and the location sensing means is an infrared digital camera.

Furthermore, in the above embodiments, preferred embodiment is, but not limited, that the location display means is optical symbols such as character, mark, figure, and pattern.

Furthermore, in the above embodiments, preferred embodiment is, but not limited, that the location display means is the sound acquisition unit itself.

Furthermore, in the above embodiments, preferred embodiment is, but not limited, that the sound acquisition unit contains a contact sensor to sense that the sound acquisition unit is placed on the simulated patient.

Furthermore, in the above embodiments, preferred embodiment is, but not limited, that when the contact sensor is sensed, the location display means turns on.

Furthermore, in the above embodiments, preferred embodiment is, but not limited, that the biological sound reproducing means is provided with a modification means being capable of modifying a repetition of a timing of reproduced respiratory sound and when predetermined biological sound information is extracted from the biological sound database to emit reproduced biological sound from the voice reproducing apparatus, a repeated timing of the reproduced respiratory sound is modulated and reproduced biological sound from the voice reproducing apparatus is emitted.

Furthermore, in the above embodiments, preferred embodiment is, but not limited, that a simulated stethoscope being provided with: a sound acquisition unit; a tube; and ear pipes, wherein the sound acquisition unit is provided with an infrared light LED as a location display means for displaying its location, at least any of the sound acquisition unit, the tube and the ear pipes is provided with a voice reproducing apparatus that emits reproduced biological sound.

Effects of the Invention

According to the present invention described above, a stethoscopy training system with simplicity and low cost can be provided. More specifically speaking, in the present invention, because a device measuring a timing of respiration operation is not used, the system becomes simple and low cost.

BEST MODE FOR CARRYING OUT THE PRESENT INVENTION

Figure 1:
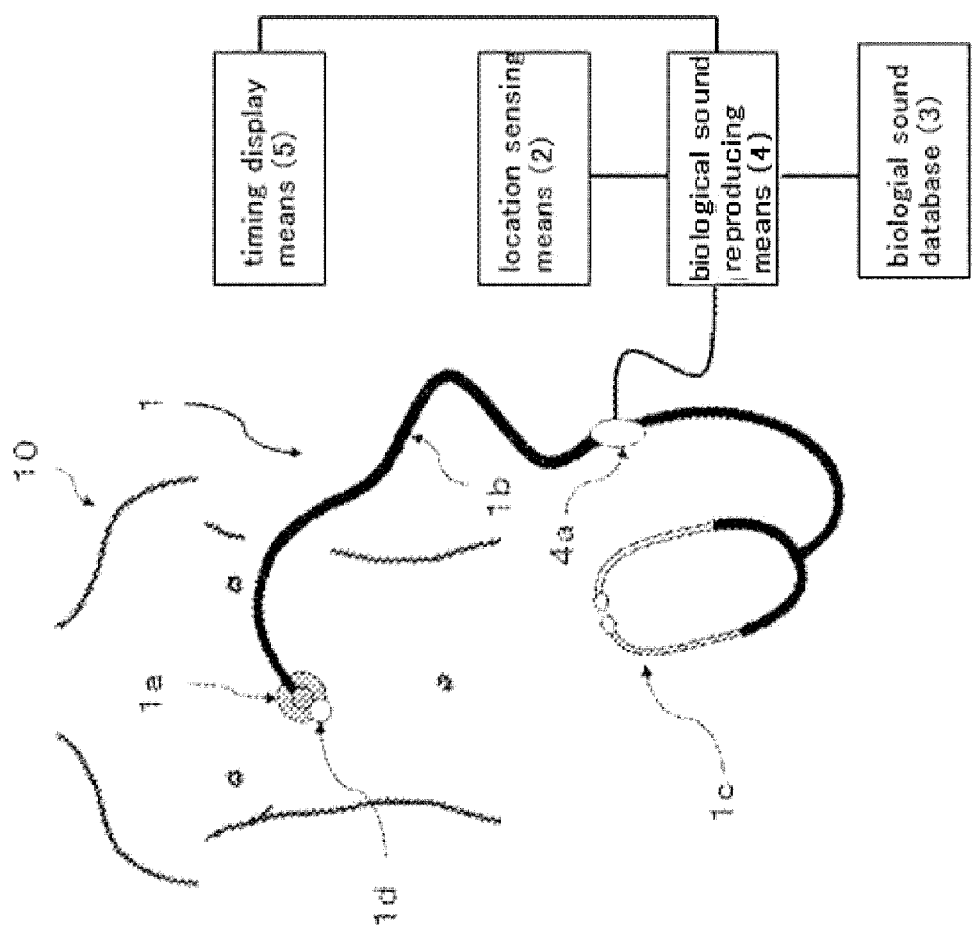
FIG. 1 is a schematic drawing for describing one example of a stethoscopy training system.
Figure 2:
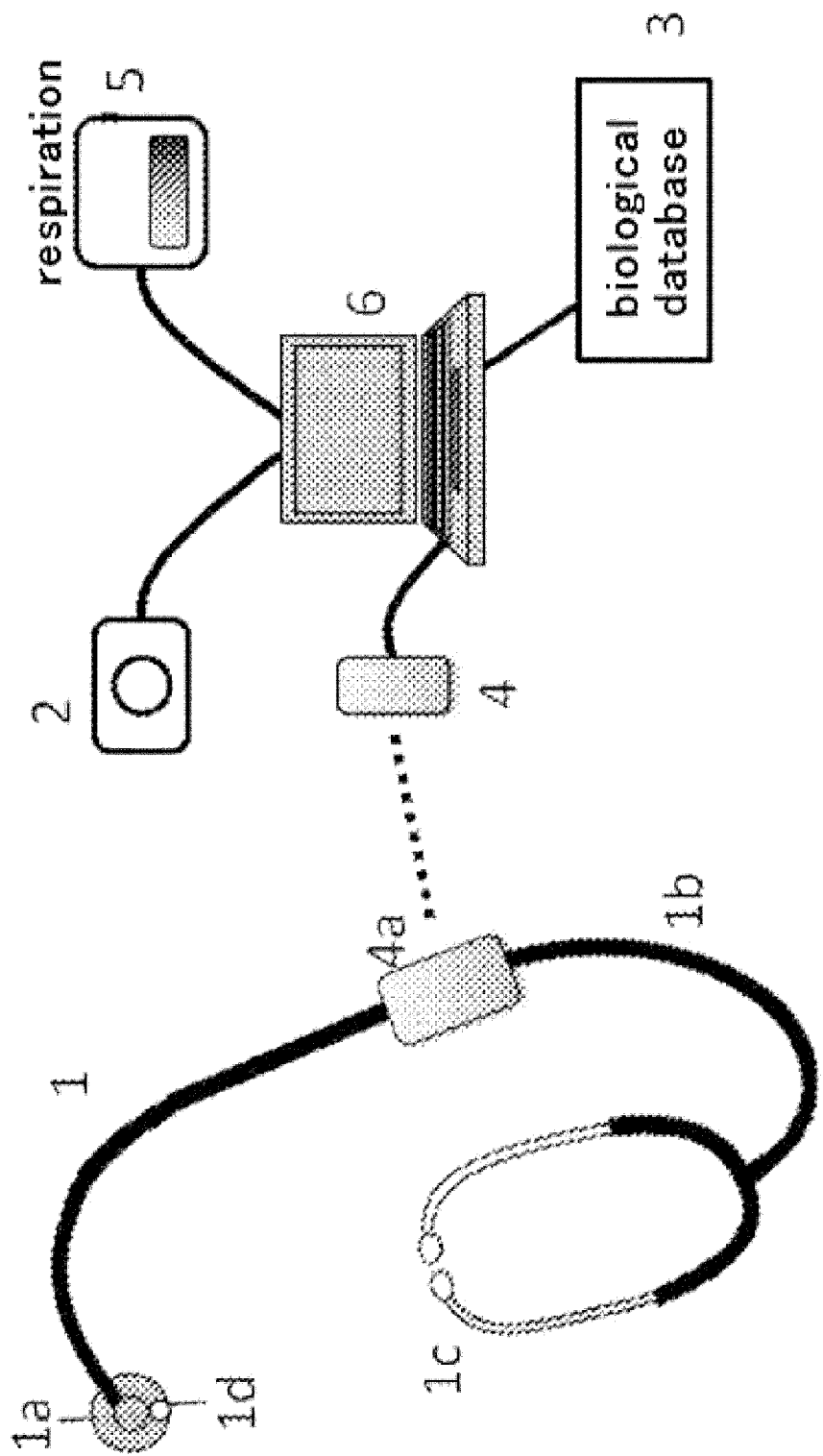
FIG. 2 is an explanatory drawing for schematically showing a configuration of a stethoscopy training system.
Figure 3:
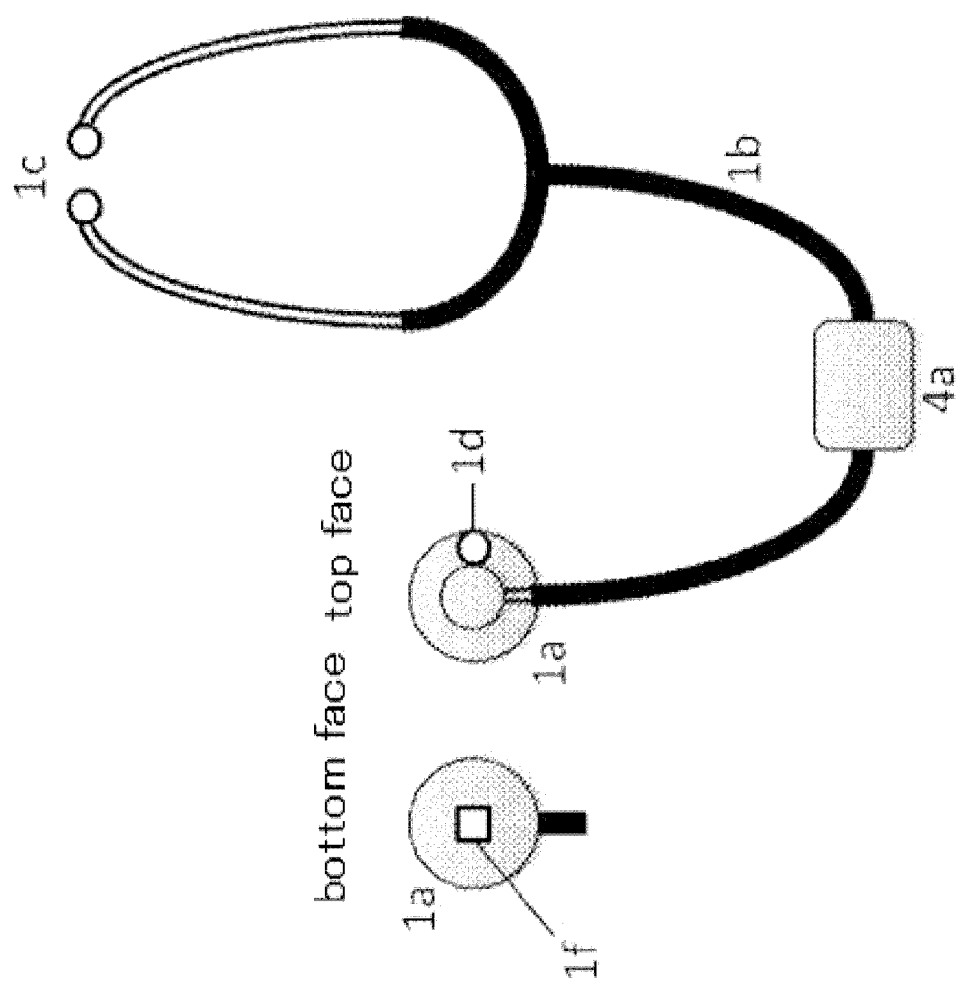
FIG. 3 is an explanatory drawing for displaying an overview configuration of a simulated stethoscope 1 for a stethoscopy training system.
Figure 4:
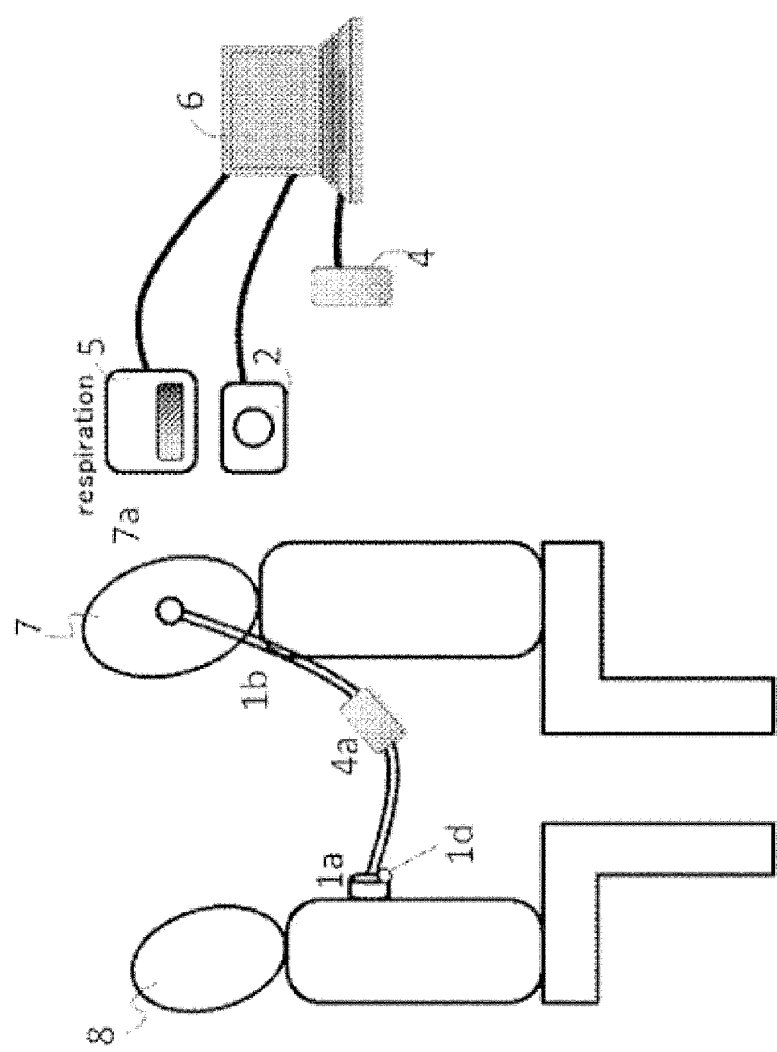
FIG. 4 is an explanatory drawing for displaying one example of usage for a stethoscopy training system.
Figure 5:
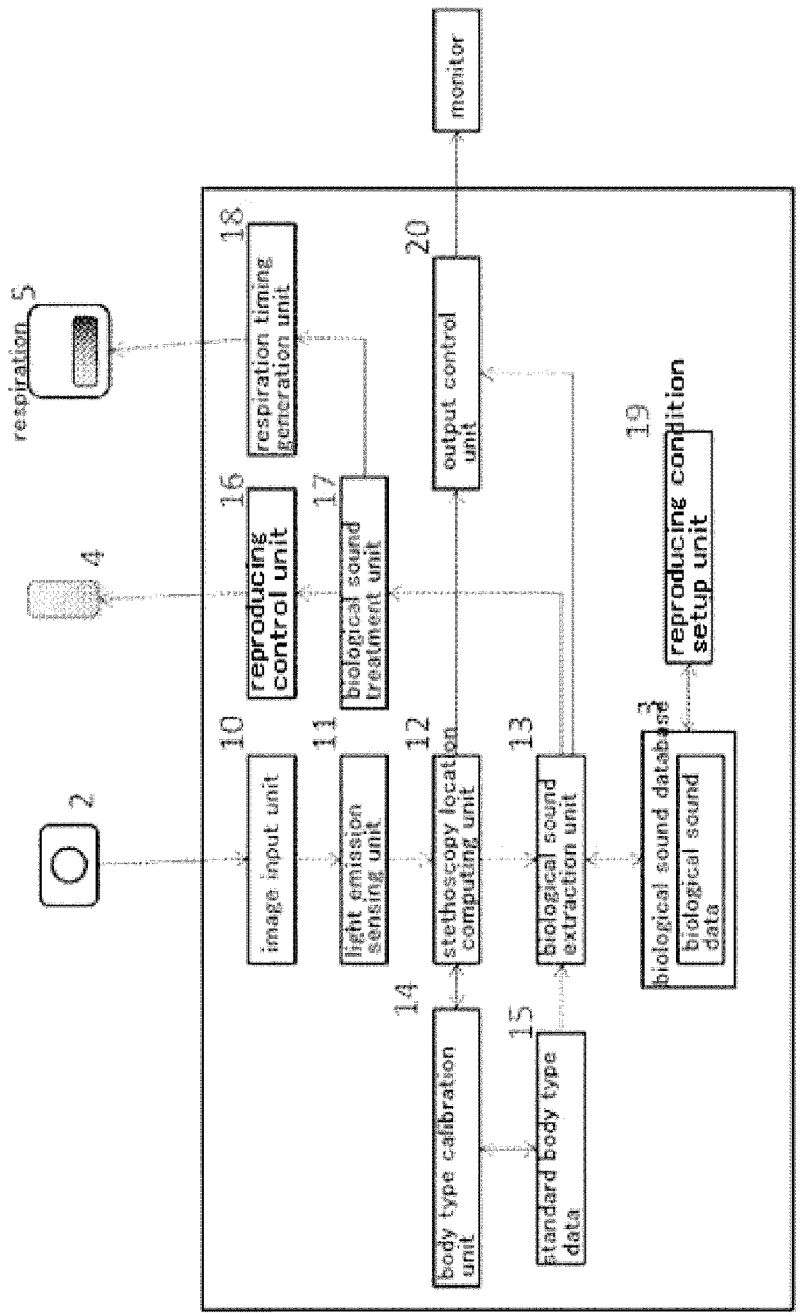
FIG. 5 is a block diagram for showing a functional configuration of a control unit.
Figure 6:
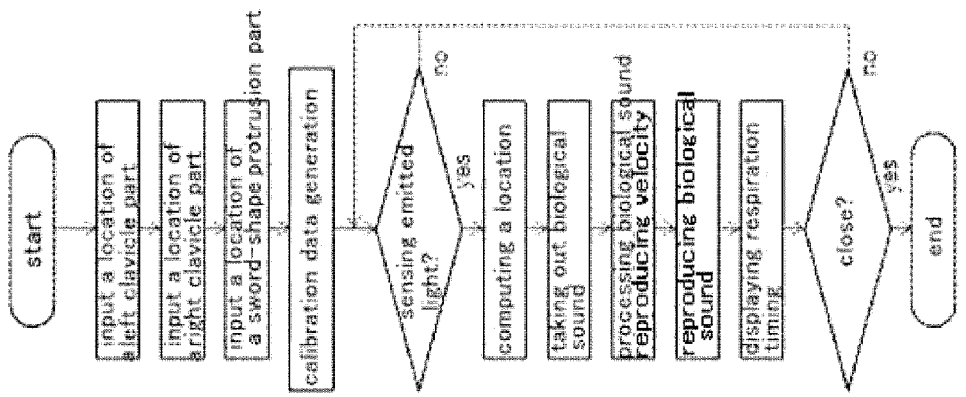
FIG. 6 is a flowchart for showing a flow of treatment of a control unit.

Hereinafter, stethoscopy training systems according to embodiments of the present invention are described based on FIG. 1 to FIG. 5. FIG. 1 is a schematic drawing for describing one example of a stethoscopy training system. FIG. 2 is an explanatory drawing for schematically showing a configuration of a stethoscopy training system according to the present embodiment. FIG. 3 is an explanatory drawing for displaying an overview configuration of a simulated stethoscope 1 for a stethoscopy training system. FIG. 4 is an explanatory drawing for displaying one example of usage for a stethoscopy training system. FIG. 5 is a block diagram for showing a functional configuration of a control unit. FIG. 6 is a flowchart for showing a flow of treatment of a control unit.

A stethoscopy training system 1 of the present embodiment, as shown in FIG. 2 to FIG. 5, is mainly provided with a simulated stethoscope 1 used for a trainee 7 performing simulated stethoscopy operation with respect to a simulated patient 8, a location sensing means 2 for sensing location of a sound acquisition unit 1a of the simulated stethoscope 1, a respiration timing presentation means 5 for presenting respiratory timing with respect to the simulated patient 8, a control unit 6 for generating suitable biological sound corresponding to location of the simulated stethoscope 1 by embedding a biological sound database 3, and a transmitting unit 4 for transmitting biological sound generated from the control unit 6 by wireless communication.

A simulated stethoscope 1, as shown in FIG. 2, is provided with a sound acquisition unit 1a having abutting stethoscopy surface with respect to body surface of a simulated patient 8, the sound acquisition unit 1a being formed by imitating shape of appearance of a stethoscope used when doctors do auscultation in a real medical site, a Y-shaped unit 1b made of soft materials, the Y-shaped unit 1b being prolonged from the sound acquisition unit 1a and being divided, a voice reproducing apparatus 4a reproducing biological sound by being mounted in the middle of the Y-shaped unit 1b and receiving biological sound wirelessly transmitted, ear pipes unit 1c mounted in each end part of the divided Y-shaped unit and is insertable into a hole of a ear of a trainee 7. Furthermore, the simulated stethoscope 1 may be formed by upgrading a portion of a real stethoscope.

The sound acquisition unit 1a of the simulated stethoscope 1, as shown in FIG. 2, is mainly provided with a abutting sensing means 1f arranging a mechanical switch for sensing abutting state of body surface by being mounted on abutting stethoscopy surface with respect to body surface of the simulated patient 8, and a location display means 1d (an infrared light LED) emitting infrared light when the sound acquisition unit 1a that is mounted on top face (back side of stethoscopy surface) of the sound acquisition unit 1a abuts on body surface.

In a location sensing means 2, in order to sense location of the sound acquisition unit 1a having a location display means 1d, two-dimensional CCD sensor in which infrared light recording is possible is used. In the sound acquisition unit 1a, abutting state is sensed by the abutting sensing means 1f with respect to body surface of the simulated patient 8. In the location display means 1d, the sound acquisition unit 1a is to be emitted only at the time of abutting state to body surface of the simulated patient 8. Thus, by the location sensing means 2 sensing emitted light of the location display means 1d, abutting state of the sound acquisition unit 1a in the location sensing means 2 with respect to body surface of the simulated patient 8 and abutting location of the sound acquisition unit 1a with respect to body surface of the simulated patient 8 can be simultaneously obtained. The location sensing means 2 transmits information to the control unit 6.

Figure 7:
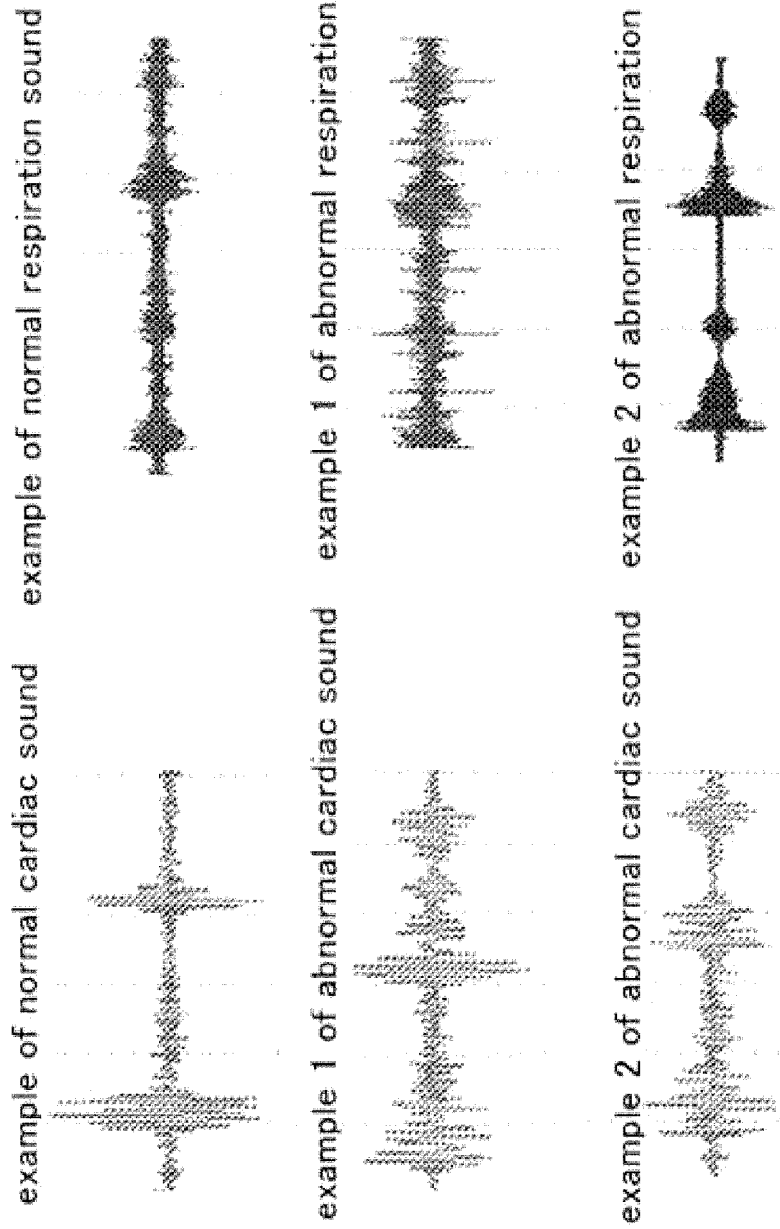
FIG. 7 is drawings for showing examples of waveforms for normal cardiac sound, abnormal cardiac sound, normal respiratory sound, and abnormal respiratory sound.

A control unit 6 is a main configuration of a stethoscopy training system of the present embodiment, control and treatment for several kinds of signals are possible according to sensed signals transmitted from the location sensing means 2, and finally it is possible to reproduce desired biological sound via the ear pipes unit 1c in the simulated stethoscope 1. The control unit 6 is provided with a biological sound memory unit 3 memorizing biological data shown in FIG. 7 reproduced from biological sound reproducing unit as shown in FIG. 4 as functional configuration by classifying into sex, age, disease, condition of patient and stethoscopy location to make database, an image input unit 10 inputting sensed image by the location sensing means 2, light emitting sensing unit 11 receiving sensed signals including information according to abutting state and a location of the sound acquisition unit 1a from the image input unit 10, a stethoscopy location computing unit 12 computing a location of the sound acquisition unit 1a from data of the light emitting sensing unit 11 and body type calibration unit, a biological sound extracting unit 13 extracting biological sound data corresponding to location of the sound acquisition unit 1a from the biological sound memory unit 3, and a play control unit 16 performing signal control for transmitting biological sound by wireless communication. Furthermore, the control unit 6, as shown in FIG. 1, can use commercial personal computer. Several kinds of manipulations and input of data can be possible by manipulation input apparatus such as keyboard and mouse.

Furthermore, the control unit 6 is provided with a biological sound treatment unit 17 independently being capable of controlling and synthesizing sound pressures and sound velocities of cardiac sound and respiratory sound to be reproduced biological sound data corresponding to sensed location of the sound acquisition unit 1a by the location sensing means 2, a respiratory timing generation unit 18 generating respiratory timing being synchronized with the biological sound treatment unit 17, a respiratory timing display means 5 presenting respiratory timing of the simulated patient 8 by compression of character and rectangle image, a reproducing condition setup unit 19 being capable of selecting several kinds of reproducing conditions such as a plurality of diseases and conditions of a patient which a trainee 7 can experience based on biological sound data memorized in the above-mentioned biological sound memory unit 3. Furthermore, the control unit 6 is provided with an output control unit 20 being capable of visibly identifying abutting state, location of the sound acquisition unit 1*a* and other kinds of information sensed by the location sensing means 2, thereby controlling and outputting signals for an output apparatus such as monitor.

In the biological sound database 3, according to the location of the sound acquisition unit 1*a*, a plurality of corresponding biological sound data is memorized. The location of the sound acquisition unit 1*a* is recorded by location information as standard of standard body type data 15. However, location of the sound acquisition unit 1*a* sensed by the location sensing means 2 is location information in body type of the simulated patient 8. Thus, it is necessary to obtain relation between standard body type recorded in the biological sound memory unit 3 and body type of the simulated patient 8. Herein, the control unit 3 obtains a location relation between central part of left and right clavicles and three points of sword-shaped protrusion to compute relation between standard body type data 15 and body type of the simulated patient 8. As a specific method, the trainee 7, as previous preparation for using the stethoscopy training system, abuts the sound acquisition unit 1*a* on the central part of left and right clavicles of the simulated patient 8 and sword-shaped protrusion in turn and the control unit 6 obtains each of location information. After obtaining location information of three points, a body type calibration unit 14 embedded in the control unit 6 computes relation between standard body type data 15 and body type of the simulated patient 8.

A biological sound reproducing means 4 can generate reproduced biological sound by using predetermined biological sound information extracted from biological sound database corresponding to location of the sound acquisition unit which the location sensing means senses through a voice reproducing apparatus 4*a* equipped with a simulated stethoscope. Furthermore, generated reproduced biological sound reaches ears of the trainee 7 through ear pipes. As a configuration of the voice reproducing apparatus 4*a*, for example, is preferably small-scaled speaker.

A respiratory timing display means 5 displays respiratory timing in a display device, etc. with respect to the simulated patient and matches respiratory operation itself with timing of reproduced respiratory sound. This point is a reverse concept and is completely different from that of prior arts described above.

Hereinabove, as described above, according to the stethoscopy training system of the present embodiment, by performing the same thing with stethoscopy operation using a conventional stethoscope with respect to the simulated patient 8, the trainee can ask condition about a patient in a determined standard procedure of an examination in internal medicine department and the trainee also smoothly perform stethoscopy corresponding to progress in several kinds of disease and condition of the patient. The trainee gets experience in the same tense place as a real medical examination. Especially, biological sound data reproduced from ear pipes unit 1*c* of the simulated stethoscope 1 is similar to biological sound when a real stethoscope is used. The trainee 7 can learn skill for stethoscopy without feeling uncomfortable by respiration of the simulated patient 8 coinciding with timing of respiratory sound reproduced as biological sound.

Hereinabove, in the present invention, preferable embodiments are described. However, the present invention is not limited to these embodiments and, as described below, several kinds of modulation and variation of design can be possible within a range that is not departing from point of the present invention.

The present embodiment shows that sensing for abutting state and a location of the sound acquisition unit 1*a* with respect to the simulated patient 8 is performed by a abutting sensing means 1*f* arranging a mechanical switch, a location display means 1*d* emitting infrared light in abutting state, and a location sensing means 2 using two-dimensional CCD sensor sensing the infrared light. However, the location sensing means 2 for specifying the stethoscopy location and the abutting sensing means 1*f* for sensing abutting state of the sound acquisition unit and body surface may be prepared in other ways.

For example, the abutting sensing means 1*f* may include a pressure sensor, a resistive film type contact sensor, an electrostatic capacitive type contact sensor, an optical type proximity sensor, and an ultrasonic type proximity sensor, etc.

Furthermore, since the sound acquisition unit 1*a* is preferably formed by imitating a sound acquisition unit of a stethoscope used by stethoscopy of doctors, it is preferable that a location display means 1*d* emitting infrared light is arranged. A location sensing means 2 using a location display means 1*d* emitting visible light and a two-dimensional CCD sensor sensing visible light can also be used. The location of the sound acquisition unit 1*a* can be specified by arranging pattern to be an indicator for sensing figure and character in the sound acquisition unit 1*a* and sensing pattern using the two-dimensional CCD sensor. However, in this case, it is necessary to prepare means transmitting abutting state of the sound acquisition unit 1*a* to the control unit 6. It is preferable to use infrared light in view of controlling effect of light emitted from environment, and moreover it is possible to modulate the location display means 1*d* such as flickering and blinking as a means for controlling effect of environmental light.

Location information along the depth can be obtained by three-dimensional location sensing device using optical type, magnetic type or mechanical type. Thus, role of the abutting sensing means 1*f* can be substituted. However, since high sensing accuracy along the depth is required to sense abutting and shape of body surface (especially, a chest part) on the simulated patient 8 is varied depending on respiratory change, it is expected to be difficult to sense abutting.

Furthermore, it was mentioned that body type calibration computes relation between standard body type and body type of the simulated patient 8 from corresponding relation between central portion of left and right clavicles and three points of sword-type protrusion. As a means for enhancing accuracy of corresponding relation therebetween, it is possible to increase numbers of corresponding location. Body type of the simulated patient 8 can be automatically sensed by analyzing image through image identification technique obtained by two-dimensional CCD sensor used as the location sensing means 2.

Furthermore, as a presentation method for timing of the respiratory timing display means 5, blinking simple substance of a light emission device as well as presenting combined character and image can be performed. It is also possible to present by utilizing sound such as voice and rhythm for the simulated patient 8. At this time, it is necessary to transmit voice only to the simulated patient 8. It is also possible to present respiratory timing to the simulated patient 8 using a small-scaled vibration device or weak electric current.

INDUSTRIAL APPLICABILITY

The present system is used for stethoscopy training that enhances stethoscopy skill for trainee such as a medical student aiming for a doctor, and a nursing student aiming for a nurse, a pharmaceutical student aiming pharmacist, a student aiming for a care person. Since stethoscopy training has a natural flow of asking condition of a patient and stethoscopy with respect to a simulated patient, the training effect is high. It is also possible to provide the system with simplicity and low cost.

DESCRIPTION OF REFERENCE NUMERALS

1—simulated stethoscope
1a—sound acquisition unit
1b—tube
1c—ear pipes
1d—location display means (for example, infrared light LED)
2—location sensing means (for example, infrared digital camera)
3—biological sound database
4—biological sound reproducing means
4a—voice reproducing apparatus (for example, small-scaled speaker)
5—timing display means

The invention claimed is:

1. A stethoscopy training system comprising:
a simulated stethoscope being provided with a sound acquisition unit, a tube and ear pipes;
a location sensing means for sensing a location of the sound acquisition unit;
a biological sound database; and
a biological sound reproducing means,
wherein when a trainee asks a simulated patient about his or her condition and auscultates the simulated patient by placing the sound acquisition unit on a chest of the simulated patient, the trainee hears a simulated biological sound reproduced from the biological sound reproducing means through the ear pipes,
wherein the sound acquisition unit has a location display means for displaying its location,
the location sensing means senses location where the sound acquisition unit is placed on a chest of the simulated patient by photographing the chest of the simulated patient and the location display means and performing image treatment,
the biological sound database retains as information biological sounds containing respiratory sound and cardiac sound previously recorded in accordance with location of a chest of an actual patient,
the biological sound reproducing means includes a voice reproducing apparatus attached to the simulated stethoscope,
the biological sound reproducing means and the voice reproducing apparatus are wiredly and wirelessly connected,
the biological sound reproducing means extracts predetermined biological sound information from the biological sound database corresponding to the location of the sound acquisition unit sensed by the location sensing means and emits reproduced biological sound from the voice reproducing apparatus, the emitted reproduced biological sound reaching ears of the trainee via the voice reproducing apparatus and the ears pipes,
furthermore, the system comprises a timing display means for displaying a repetition of a timing of reproduced respiratory sound,
the simulated patient can match his respiratory operation with a timing of a respiratory sound in the reproduced biological sound by observing the timing display means.

2. The stethoscopy training system according to claim 1, wherein the location display means is an infrared light LED and the location sensing means is an infrared digital camera.

3. The stethoscopy training system according to claim 1, wherein the location display means is optical symbols such as character, mark, figure, and pattern.

4. The stethoscopy training system according to claim 1, wherein the location display means is the sound acquisition unit itself.

5. The stethoscopy training system according to claim 1, wherein the sound acquisition unit contains a contact sensor to sense that the sound acquisition unit is placed on the simulated patient.

6. The stethoscopy training system according to claims 5, wherein when the contact sensor is sensed, the location display means turns on.

7. The stethoscopy training system according to claim 1, wherein the biological sound reproducing means is provided with a modification means being capable of modifying a repetition of a timing of reproduced respiratory sound and when predetermined biological sound information is extracted from the biological sound database to emit the reproduced biological sound from the voice reproducing apparatus, a repeated timing of the reproduced respiratory sound is modulated and the reproduced biological sound from the voice reproducing apparatus is emitted.

8. A stethoscopy training system comprising:
a simulated stethoscope being provided with a sound acquisition unit, a tube and ear pipes;
a location sensing means for sensing a location of the sound acquisition unit;
a biological sound database;
a biological sound reproducing means; and
a timing display means for displaying a repetition of a timing of reproduced respiratory sound,
wherein the sound acquisition unit has a location display means for displaying its location,
the location sensing means senses a location where a sound acquisition unit is placed on a chest of the simulated patient by photographing a chest of the patient and the location display means and performing image treatment,
the biological sound database retains as information biological sounds containing respiratory sound and cardiac sound previously recorded in accordance with location of a chest of an actual patient,
the biological sound reproducing means includes a voice reproducing apparatus attached to the simulated stethoscope,
the biological sound reproducing means and the voice reproducing apparatus are wiredly and wirelessly connected,
the biological sound reproducing means extracts predetermined biological sound information from the biological sound database corresponding to the location of the sound acquisition unit sensed by the location sensing means and emits reproduced biological sound from the voice reproducing apparatus, the emitted reproduced biological sound reaching ears of the trainee via the voice reproducing apparatus and the ears, the timing displays means is formed so that the simulated patient can match respiratory operation with a timing of respiratory sound in the reproduced biological sound by observing the timing display means.

9. The stethoscopy training system according to claim 8, wherein the location display means is an infrared light LED and the location sensing means is an infrared digital camera.

10. The stethoscopy training system according to claim 8, wherein the location display means is optical symbols such as character, mark, figure, and pattern.

11. The stethoscopy training system according to claim 8, wherein the location display means is the sound acquisition unit itself.

12. The stethoscopy training system according to claim 8, wherein the sound acquisition unit contains a contact sensor to sense that the sound acquisition unit is placed on the simulated patient.

13. The stethoscopy training system according to claim 12, wherein when the contact sensor is sensed, the location display means turns on.

14. The stethoscopy training system according to claim 8, wherein the biological sound reproducing means is provided with a modification means being capable of modifying a repetition of a timing of reproduced respiratory sound and when predetermined biological sound information is extracted from the biological sound database to emit the reproduced biological sound from the voice reproducing apparatus, a repeated timing of the reproduced respiratory sound is modulated and the reproduced biological sound from the voice reproducing apparatus is emitted.

* * * * *